United States Patent
Iseberg et al.

(10) Patent No.: US 9,989,434 B2
(45) Date of Patent: Jun. 5, 2018

(54) SYSTEM AND METHOD FOR PROVIDING AN APPLIED FORCE INDICATION

(71) Applicant: ETYMOTIC RESEARCH, INC., Elk Grove Village, IL (US)

(72) Inventors: Steve Iseberg, Crystal Lake, IL (US); Jerrold Zdenek, Deer Park, IL (US); James Collins, Elk Grove Village, IL (US); Gail Gudmundsen, Elk Grove Village, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 613 days.

(21) Appl. No.: 14/562,025

(22) Filed: Dec. 5, 2014

(65) Prior Publication Data

US 2015/0160090 A1 Jun. 11, 2015

Related U.S. Application Data

(60) Provisional application No. 61/913,712, filed on Dec. 9, 2013.

(51) Int. Cl.
*G01L 27/00* (2006.01)
*A61B 5/12* (2006.01)
(Continued)

(52) U.S. Cl.
CPC .......... *G01L 27/002* (2013.01); *A61B 5/123* (2013.01); *G01L 1/02* (2013.01); *H04R 25/30* (2013.01); *H04R 2460/13* (2013.01)

(58) Field of Classification Search
CPC ........ G01L 27/002; A61B 5/123; H04R 25/30
See application file for complete search history.

(56) References Cited

U.S. PATENT DOCUMENTS 2,062,372 A * 12/1936 Nicholides ............. H04R 11/02
381/151
2,459,325 A  1/1949 Knowles
(Continued)

FOREIGN PATENT DOCUMENTS

DE  10 2011 010 423   8/2012
WO     2008/139404   11/2008

OTHER PUBLICATIONS

PCT Notification of Transmittal of the International Search Report and the Written Opinion of the International Search Authority, dated Jun. 23, 2016, 9 pages.
(Continued)

*Primary Examiner* — Sean Dougherty
(74) *Attorney, Agent, or Firm* — McAndrews, Held & Malloy, Ltd.

(57) ABSTRACT

Certain embodiments provide a system and method for measurement of the force applied to a bone-conduction oscillator during application to a subject, resolving the measured force relative to a pre-determined criteria, and providing an indication to the user to specify whether an external force applied to an applied force indication system coupled with a bone-conduction oscillator is within a pre-determined acceptable range. A mechanical arrangement is prescribed which allows the full extent of the force applied to be represented onto the pressure measurement apparatus. The system and apparatus may be applied onto or integrated into bone-conduction oscillators.

28 Claims, 7 Drawing Sheets

(51) Int. Cl.
*H04R 25/00* (2006.01)
*G01L 1/02* (2006.01)

(56) References Cited

U.S. PATENT DOCUMENTS

| | | | | |
|---|---|---|---|---|
| 4,195,643 | A * | 4/1980 | Pratt, Jr. | A61B 5/1036 600/592 |
| 4,217,912 | A * | 8/1980 | Hubmann | A61B 5/02007 600/552 |
| 4,340,409 | A * | 7/1982 | Brooks | G01L 7/102 361/283.4 |
| 4,784,152 | A * | 11/1988 | Shinoda | A61B 5/021 600/503 |
| 4,951,671 | A * | 8/1990 | Coan | A61B 3/16 600/405 |
| 5,179,956 | A * | 1/1993 | Harada | A61B 5/02233 600/485 |
| 5,749,363 | A * | 5/1998 | Ishii | A61B 8/0875 600/453 |
| 5,766,137 | A * | 6/1998 | Omata | A61B 5/02007 600/587 |
| 5,788,656 | A * | 8/1998 | Mino | A61F 11/00 601/47 |
| 6,117,086 | A * | 9/2000 | Shulze | A61B 5/0215 600/486 |
| 6,478,051 | B1 * | 11/2002 | Drumm | F15B 1/033 138/30 |
| 6,609,426 | B1 * | 8/2003 | Altmann | G01L 9/0051 73/715 |
| 7,043,040 | B2 * | 5/2006 | Westerkull | H04R 25/606 381/181 |
| 7,292,695 | B2 * | 11/2007 | Kobayashi | H04R 9/10 381/151 |
| 7,682,303 | B2 * | 3/2010 | Abolfathi | H04R 25/604 181/128 |
| 7,722,542 | B2 * | 5/2010 | Lia | A61B 5/021 600/485 |
| 7,772,657 | B2 * | 8/2010 | Vaganov | G01L 1/044 257/415 |
| 8,023,676 | B2 * | 9/2011 | Abolfathi | A61B 5/0028 381/151 |
| 8,160,279 | B2 * | 4/2012 | Abolfathi | H04R 25/554 381/151 |
| 8,270,638 | B2 * | 9/2012 | Abolfathi | G01P 1/127 381/151 |
| 8,384,551 | B2 * | 2/2013 | Ross | A43B 3/0005 340/573.1 |
| 8,491,509 | B2 * | 7/2013 | Trandafir | A61H 1/001 600/595 |
| 8,542,857 | B2 * | 9/2013 | Åsnes | H04R 25/606 381/326 |
| 9,113,277 | B2 * | 8/2015 | Ball | H04R 25/606 |
| 9,749,758 | B2 * | 8/2017 | Puria | H04R 25/606 |
| 2002/0069883 | A1 * | 6/2002 | Hirchenbain | A61F 11/06 128/867 |
| 2003/0212335 | A1 * | 11/2003 | Huang | A61B 5/021 600/500 |
| 2004/0037428 | A1 * | 2/2004 | Keller | A61B 5/121 381/60 |
| 2005/0065634 | A1 * | 3/2005 | Nakajima | H01L 21/67248 700/213 |
| 2005/0113691 | A1 * | 5/2005 | Liebschner | A61B 5/4504 600/437 |
| 2005/0177047 | A1 * | 8/2005 | Harpas | A61B 5/0053 600/485 |
| 2006/0258960 | A1 * | 11/2006 | Turnbull | A61B 90/06 600/587 |
| 2007/0041595 | A1 * | 2/2007 | Carazo | H04R 17/00 381/151 |
| 2007/0073232 | A1 * | 3/2007 | Pickhard | A61M 5/2033 604/134 |
| 2007/0233421 | A1 * | 10/2007 | Scholz | G01D 3/022 702/138 |
| 2008/0214372 | A1 * | 9/2008 | Karp | A61B 5/224 482/140 |
| 2009/0285417 | A1 * | 11/2009 | Shin | H04M 1/03 381/151 |
| 2010/0098269 | A1 * | 4/2010 | Abolfathi | G01S 19/18 381/151 |
| 2011/0054353 | A1 * | 3/2011 | Hulvershorn | A61B 5/032 600/587 |
| 2011/0066010 | A1 * | 3/2011 | Moon | A61B 5/0205 600/301 |
| 2011/0092818 | A1 * | 4/2011 | Sarvazyan | A61B 8/0875 600/449 |
| 2011/0270014 | A1 | 11/2011 | Flynn et al. | |
| 2013/0089229 | A1 | 4/2013 | Kristo et al. | |
| 2013/0233085 | A1 * | 9/2013 | Mizoguti | G01L 13/025 73/716 |
| 2013/0281897 | A1 * | 10/2013 | Hoffmann | A61B 8/08 601/107 |
| 2014/0144243 | A1 * | 5/2014 | Tanaka | G01L 13/025 73/716 |
| 2015/0007650 | A1 * | 1/2015 | Rose | E21B 47/06 73/152.51 |
| 2015/0330854 | A1 * | 11/2015 | Tsushima | G01L 13/026 73/717 |
| 2016/0128623 | A1 * | 5/2016 | Bhat | A61B 5/447 600/301 |

OTHER PUBLICATIONS

Cone-Wesson, B., "Bone-Conduction ABR Tests," American Journal of Audiology, vol. 4(3), Nov. 1995, pp. 14-19.
Hakansson, B.E., "The Balanced Electromagnetic Separation Transducer: A New Bone Conduction Tansducer," Journal Acoustical Society of America, vol. 113(2), Feb. 2003, pp. 818-825.
Hansen E.E. and Small, S.A., "Effective Masking Levels for Bone Conduction Auditory Steady State Responses in Infants and Adults with Normal Hearing," Ear & Hearing, vol. 33(2), 2012, pp. 257-266.
Ho, E.C., et al., "Bilateral Bone-Anchored Hearing Aid: Impact on Quality of Life Measured with the Glasgow Benefit Inventory," Otology & Neurotology, vol. (30)7, 2009, pp. 891-896.
Popelka, G.R., et al., "Preliminary Evaluation of a Novel Bone-Conduction Device for Single-Sided Deafness," Otology & Neurotology, vol. 31(3), 2010, pp. 492-497.
Small, S.A., et al., "Effects of Bone Oscillator Coupling Method, Placement Location, and Occlusion on Bone-Conduction Auditory Steady-State Responses in Infants," Ear & Hearing, vol. 28(1), Feb. 2007, pp. 83-98.
Stapells, D.R.. and Ruben, R.J., "Auditory Brain Stem Responses to Bone-Conducted Tones in Infants," Annals of Otology, Rhinology & Laryngology, vol. 98(12), Dec. 1989, pp. 941-949.
Stapells, D.R., "Low-Frequency Hearing and the Auditory Brainstem Response," American Journal of Audiology, Jul. 1994, pp. 11-13.
Stapells, D.R., "Threshold Estimation by the Tone-Evoked Auditory Brainstem Response: A Literature Meta-Analysis," Journal of Speech-Language Pathology and Audiology, vol. 24(2), Jun. 2000, pp. 74-83.
Tjellstrom, A., "Bone-Anchored Hearing Aids: from a test project to an established clinical routine," ENT & Audiology News, vol. 19(1), Mar./Apr. 2010, pp. 38-40.
Toll, L.E., et al., "Effect of static force on bone conduction hearing thresholds and comfort," International Journal of Audiology, 2011, vol. 50, pp. 632-635.
Vander Werff, K.R., et al., "Infant Air and Bone Conduction Tone Burst Auditory Brain Stem Responses for Classification of Hearing Loss and the Relationship to Behavioral Thresholds," Ear & Hearing, vol. 30(3), 2009, pp. 350-368.
Wilber, L.A., "Pure Tone Audiometry: Air and Bone Conduction," Chapter 2 in Handbook of Clinical Audiology. Katz J (ed), Lippincott Williams & Wilkins, 4th ed., 1994, pp. 29-49.
Yang, E.Y., et al., "Effect of Vibrator to Head Coupling Force on the Auditory Brain Stem Response to Bone Conducted Clicks in Newborn Infants," Ear & Hearing, vol. 12(1), 1991, pp. 55-60.

(56) References Cited

OTHER PUBLICATIONS

Yang, E.Y. and Stuart, A., "The Contribution of the Auditory Brainstem Responses to Bone-Conducted Stimuli in Newborn Hearing Screening." Journal of Speech-Language Pathology and Audiology, vol. 24(2), Jun. 2000, pp. 84-91.
International Search Report and Written Opinion for International Patent Application No. PCT/US2014/68816, dated Mar. 10, 2015.

* cited by examiner

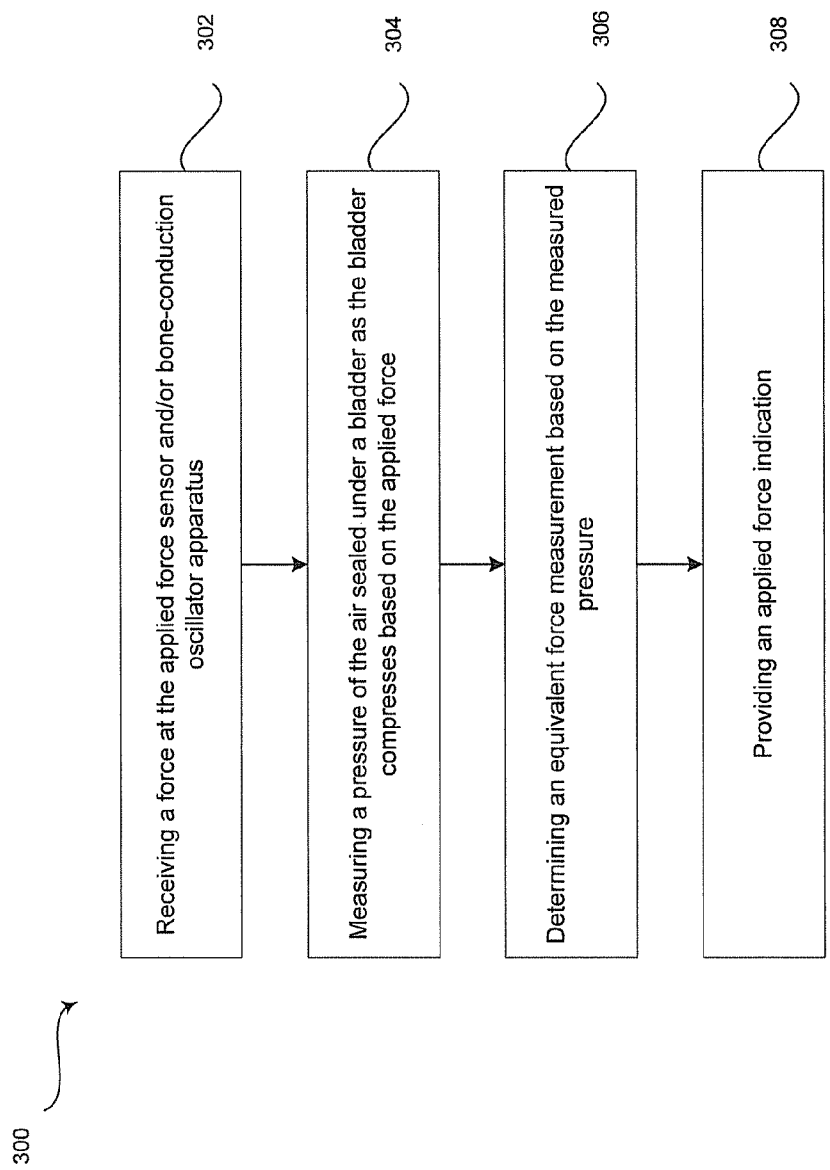

SYSTEM AND METHOD FOR PROVIDING AN APPLIED FORCE INDICATION

CROSS-REFERENCE TO RELATED APPLICATIONS/INCORPORATION BY REFERENCE

The present application claims priority under 35 U.S.C. § 119(e) to provisional application Ser. No. 61/913,712 filed on Dec. 9, 2013, entitled "System and Method for Providing an Applied Force Indication." The above referenced provisional application is hereby incorporated herein by reference in its entirety.

FIELD OF THE INVENTION

Certain embodiments of the invention relate to audiometric and/or auditory brainstem response (ABR) hearing tests provided using a bone-conduction oscillator. More specifically, certain embodiments of the invention relate to a system and method for providing an indication of applied force to specify whether the force applied to a bone-conduction oscillator is within a range sufficient to obtain reliable audiometric and/or auditory brainstem response (ABR) hearing test results.

BACKGROUND OF THE INVENTION

Audiometry is the testing of function of the hearing mechanism, including mechanical sound transmission tests (middle ear function), neural sound transmission tests (cochlear function), and speech discrimination ability tests (central integration). Typically, a complete evaluation of a patient's hearing is done by trained personnel using instruments designed specifically for hearing testing. In conventional audiometric hearing testing, an audiometer generates pure tones (single frequencies) to test air and bone conduction. The audiometer includes a pure tone generator, an oscillator for bone conduction testing, an attenuator for varying loudness, a microphone for speech testing, and earphones for air conduction testing. Other hearing tests include auditory brainstem response (ABR), which measures neural transmission time and amplitude from the cochlea through the brainstem.

Pure tone audiometric bone conduction testing is performed by presenting a pure tone to the ear through an oscillator placed on the mastoid and measuring threshold (i.e., the lowest intensity in decibels (dB) at which the pure tone is perceived 50% of the time). For auditory brainstem response (ABR) audiometry, electrodes are placed on the patient's vertex, earlobes, and forehead. Auditory brainstem responses (ABRs) produced in response to air and bone conduction stimuli may provide frequency-specific hearing thresholds. The air and bone conduction ABR thresholds, similar to typical behavioral audiometric testing, provide diagnostic information that differentiates between conductive, sensorineural, and mixed hearing losses. ABR testing can be used to assess patients, such as young children, infants, and difficult to test patients that cannot be evaluated with conventional behavioral audiometric testing.

FIG. 1 is a top, side perspective view of a bone-conduction oscillator 100 as is known in the art. Referring to FIG. 1, there is shown a bone-conduction oscillator 100 comprising a housing 110 and a cable 120. The cable may be operable to provide the bone-conduction stimuli from the audiometer and/or auditory brainstem response (ABR) equipment, for example. The housing 110 can include a detent 112 for attaching to a headband. For example, typical bone-conduction oscillators are commonly placed on a patient using metal headbands. Some researchers recommend using a spring-scale to measure the coupling force of the headband to a head of a patient to control the force applied to the bone-conduction oscillator 100.

In conventional audiometric bone conduction testing and auditory brainstem response (ABR) testing, one concern is that the amount of force applied to the bone-conduction oscillator 100 is consistent and within an appropriate range. The amount of force applied to the bone-conduction oscillator is proportional to the efficiency of the transmission of the stimulus from the oscillator to the bone. Too much pressure, too little pressure, or variations in pressure during the presentation of a stimulus can cause a greater degree of uncertainty in the measurements taken. Coupling the oscillator 100 to a head of an infant using a headband is a commonly suggested clinical method for performing auditory brainstem response (ABR) testing because a force can be applied by the headband and the amount of force can be verified. However, current commercially available headbands for bone-conduction oscillators do not allow one to regulate and monitor static pressure. This becomes an even more difficult problem with the smaller heads of children. Another method used in a clinical setting is to hold the bone-conduction oscillator 100 in place by hand because it is more comfortable for an infant and is faster and less likely to wake the infant than positioning a headband. However, the hand-held method has generally been discouraged due to the potential for the applied force to be outside an appropriate range and/or to vary during testing, resulting in an inconsistent output from the transducer, which can potentially produce inaccurate thresholds.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for providing an indication of applied force, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

BRIEF DESCRIPTION OF SEVERAL VIEWS OF THE DRAWINGS

FIG. 7 is a flow chart illustrating exemplary steps that may be utilized for providing an applied force indication to specify whether a force applied to a bone-conduction oscillator is sufficient to obtain reliable audiometric and/or auditory brainstem response (ABR) hearing test results, in accordance with an embodiment of the invention.

DETAILED DESCRIPTION OF THE INVENTION

Certain embodiments of the invention may be found in a system and method for providing an applied force indication to specify whether the force applied to a bone-conduction oscillator is within a range sufficient to obtain reliable audiometric and/or auditory brainstem response (ABR) hearing test results.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the terms microcontroller, processor, or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein include an applied force indication system attached to or coupled with a bone-conduction oscillator. As used herein, the terms "attached to" and "coupled with" should be understood as not excluding an applied force indication system integrated with a bone-conduction oscillator unless such exclusion is explicitly stated.

Figure 2:
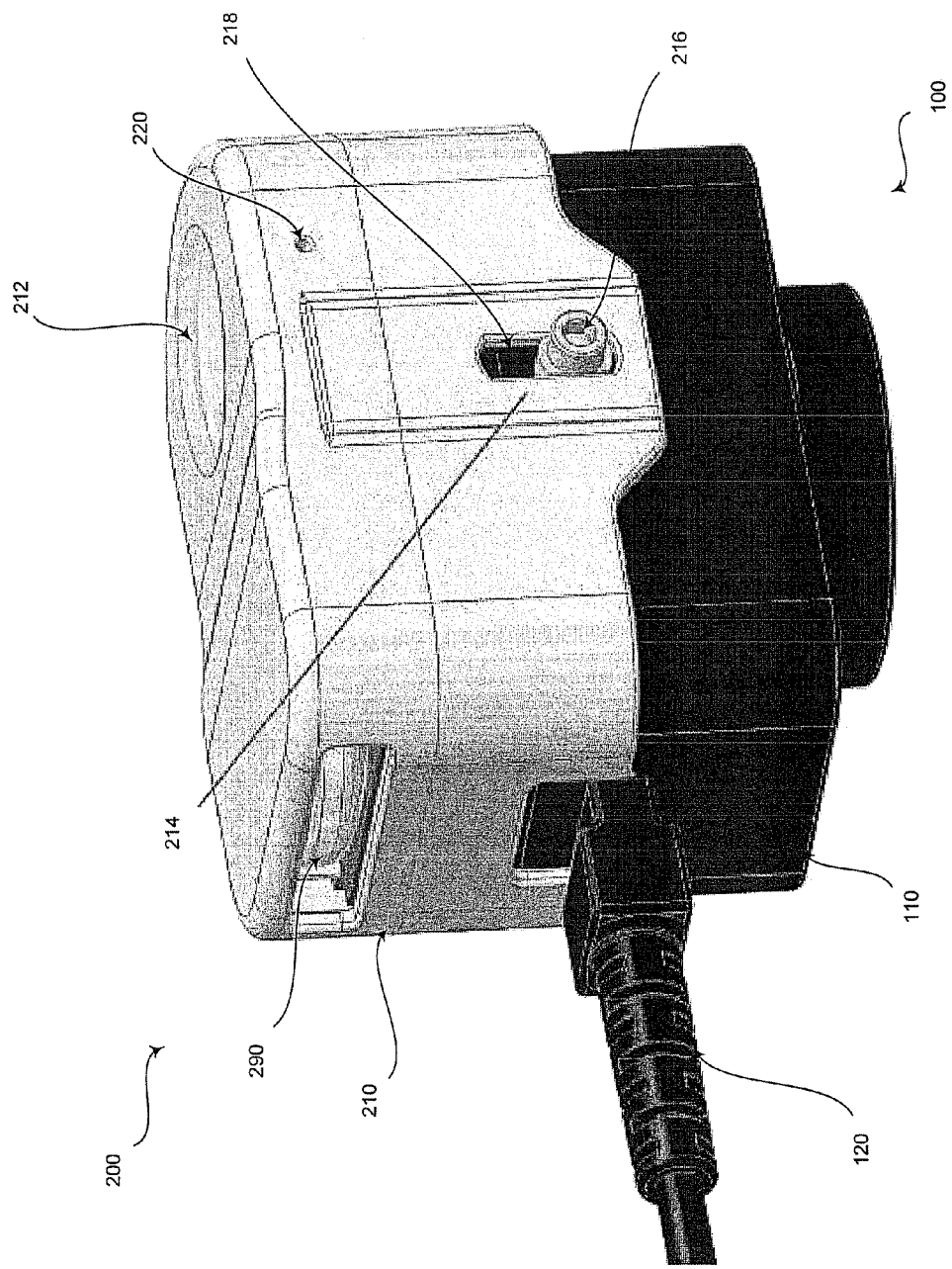
FIG. 2 is a back, side perspective view of an exemplary applied force indication system attached to a bone-conduction oscillator, in accordance with an embodiment of the invention.

FIG. 2 is a back, side perspective view of an exemplary applied force indication system 200 attached to a bone-conduction oscillator 100, in accordance with an embodiment of the invention. Referring to FIG. 2, there is shown an applied force indication system 200 and a bone-conduction oscillator 100.

The bone-conduction oscillator 100 comprises a housing 110 and a cable 120. The bone-conduction oscillator 100 is operable to provide bone-conduction stimuli to a skull of a patient. The bone-conduction stimuli can be provided to the oscillator 100 from an audiometer and/or auditory brainstem response (ABR) equipment via cable 120, for example.

Figure 4:
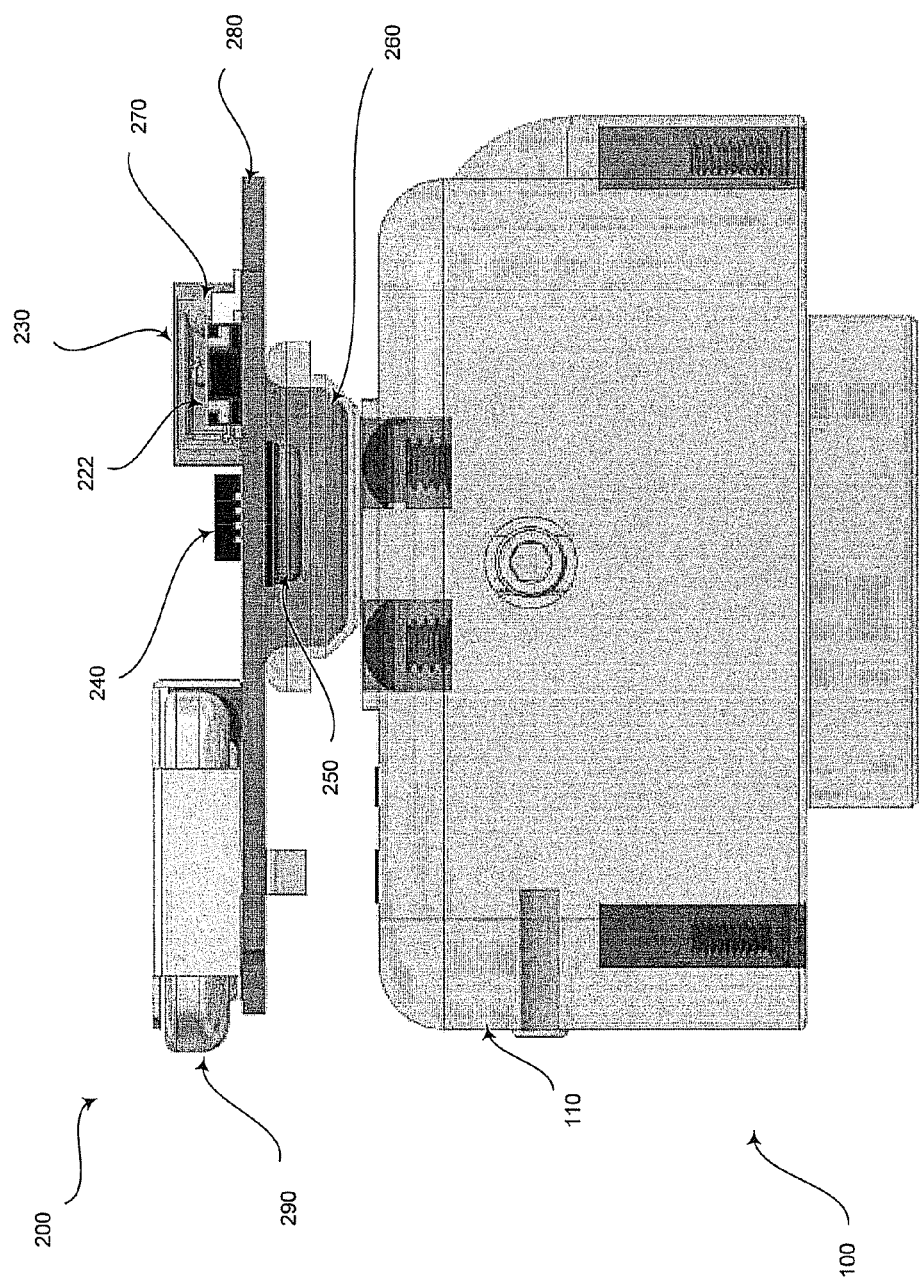
FIG. 4 is a side elevation view of an exemplary applied force indication system without a housing and attached to a bone-conduction oscillator, in accordance with an embodiment of the invention.
Figure 5:
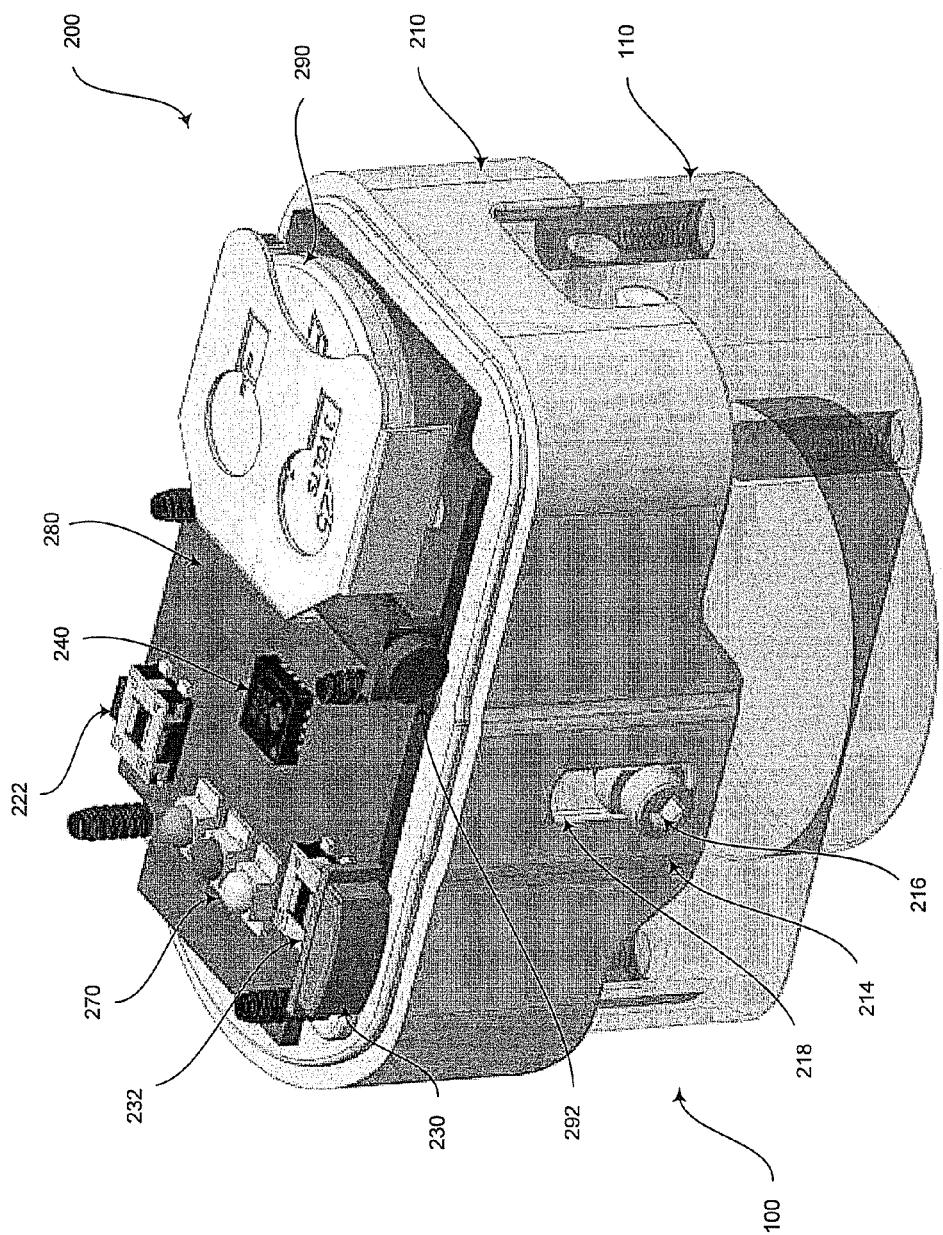
FIG. 5 is a side perspective view of an exemplary applied force indication system without a portion of the housing and attached to a bone-conduction oscillator, in accordance with an embodiment of the invention.
Figure 6:
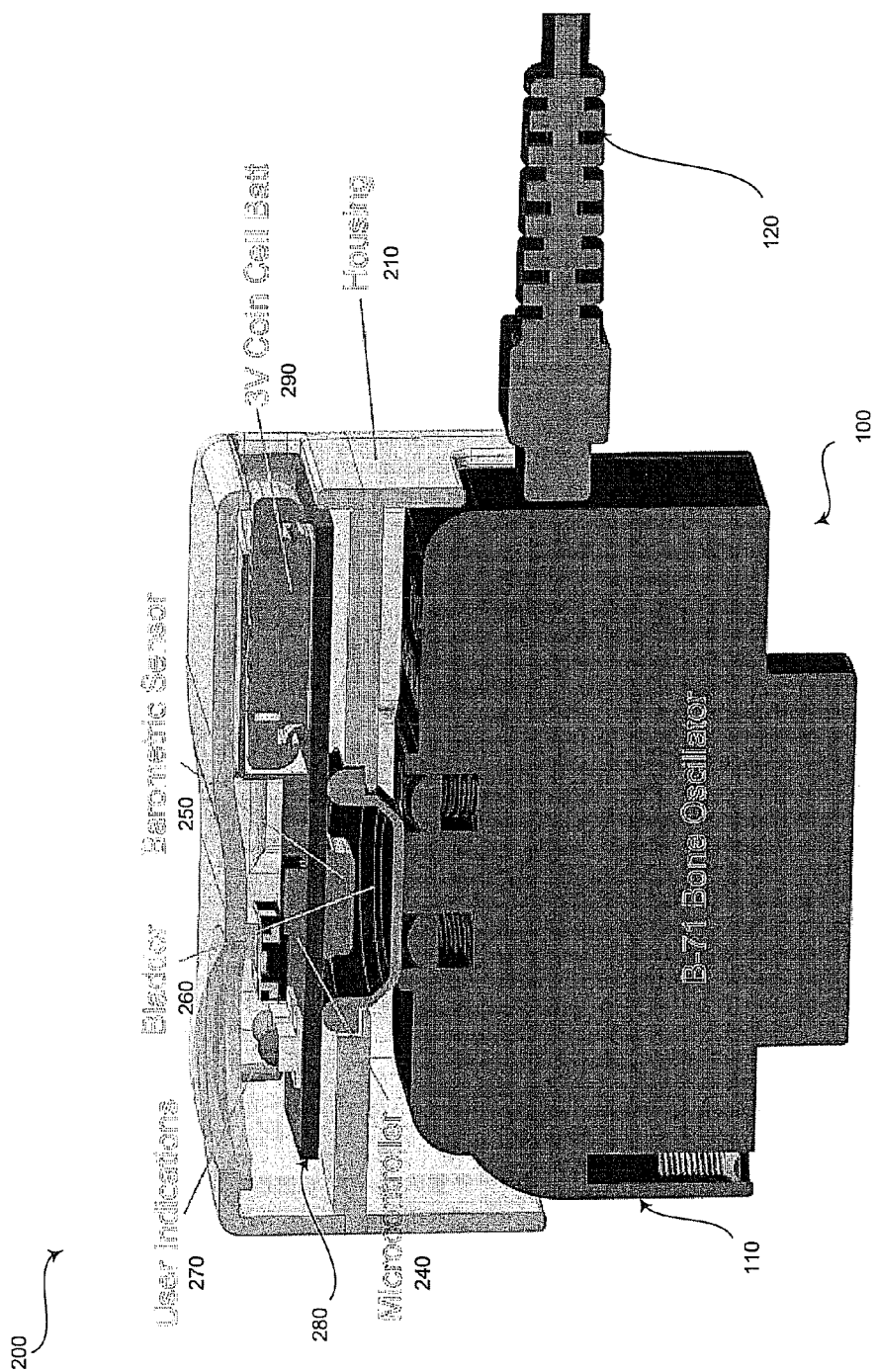
FIG. 6 is a side sectional view of an exemplary applied force indication system attached to a bone-conduction oscillator, in accordance with an embodiment of the invention.

The applied force indication system 200 comprises a housing 210, attachment mechanisms 214, a calibration switch aperture 220, and a battery 290. In various embodiments, the housing can include an indicator viewing opening or window 212 for viewing indicators 270 as illustrated in FIGS. 4-6 and described in more detail below.

The attachment mechanisms 214 may be pin 216 and slot 218 arrangements, or any suitable attachment mechanisms.

Figure 1:
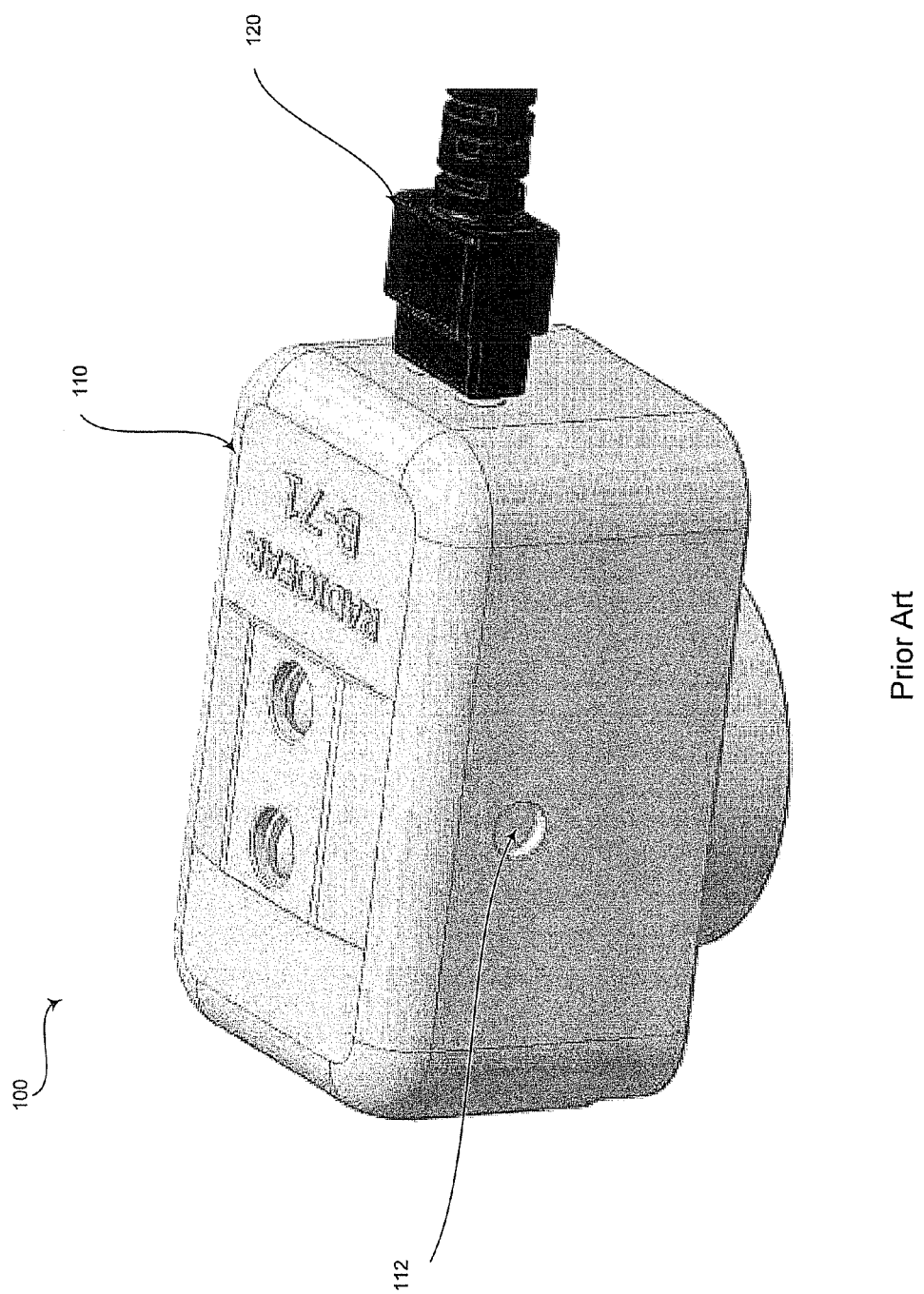
FIG. 1 is a top, side perspective view of a bone-conduction oscillator 100 as is known in the art.

The pin 216 and slot 218 arrangements can allow the system 200 to pivot within and freely slide along the slot 218. For example, the unrestricted coupling provided by the slot 218 in conjunction with pin 216, or other suitable attachment mechanism 214, allows the force indication system 200 to move freely in the vertical axis as well as radially to the pin 216. In an exemplary embodiment, the pins 216 may fit into the detents 112 of the bone-conduction oscillator 100, as illustrated in FIG. 1, to couple or integrate the applied force indication system 200 with the bone-conduction oscillator 100.

The calibration switch aperture 220 can provide access via a pen, paper clip, or any suitable device, to a calibration switch 222 used during a calibration process and disposed within the housing 210. In certain embodiments, the calibration switch 222 can be a momentary switch, a toggle switch, or any suitable switch.

The battery 290 is disposed within the housing 210 and is operable to provide power to the electronic components of the applied force indication system 200 as described in more detail below. In various embodiments, the battery 290 may be a 3-volt coin cell or any suitable battery for providing power to the applied force indication system 200.

Figure 3:
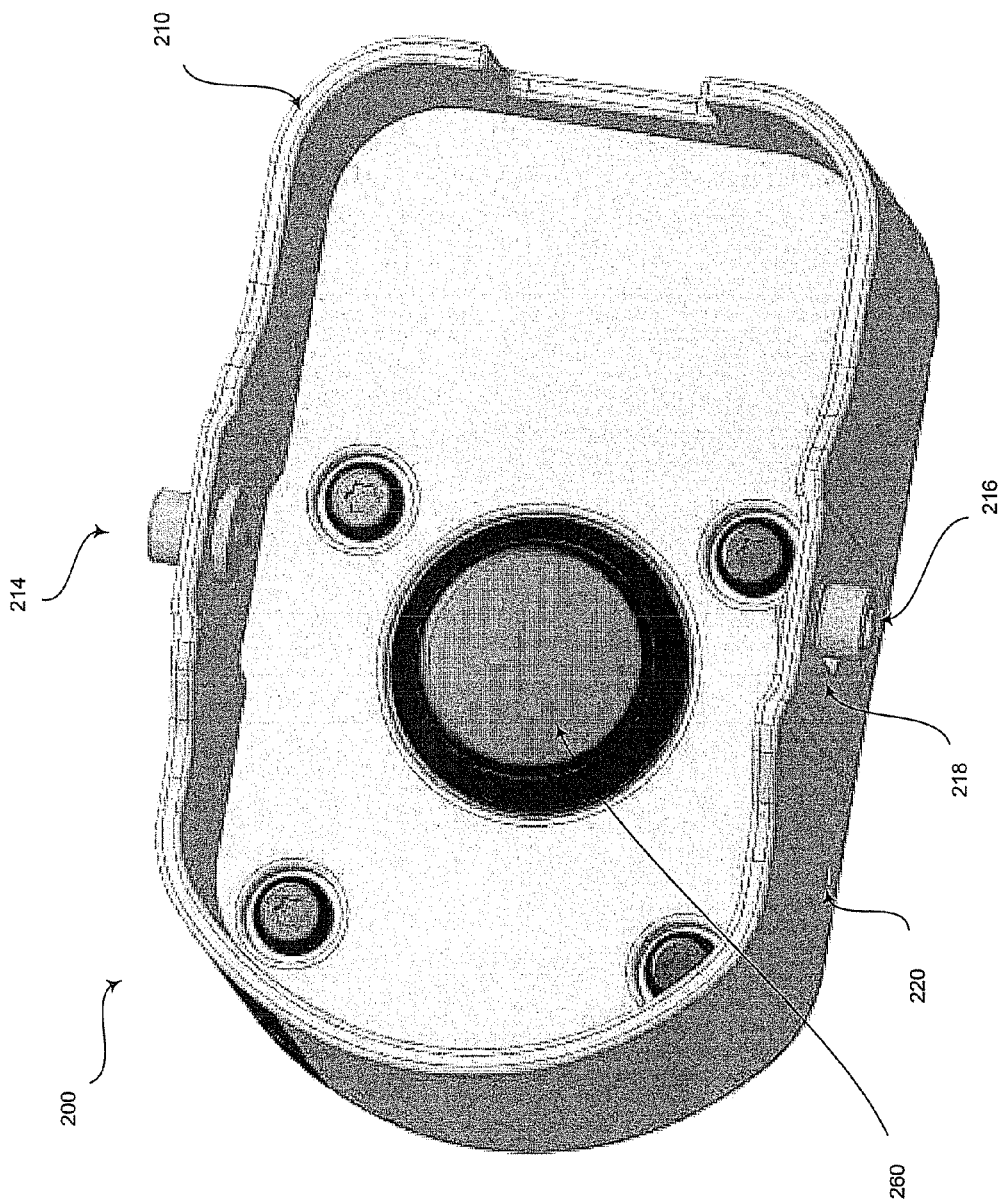
FIG. 3 is a bottom perspective view of an exemplary applied force indication system, in accordance with an embodiment of the invention.

FIG. 3 is a bottom perspective view of an exemplary applied force indication system 200, in accordance with an embodiment of the invention. Referring to FIG. 3, there is shown an applied force indication system 200. The applied force indication system 200 comprises a housing 210, attachment mechanisms 214, a calibration switch aperture 220, and a force measurement device 260.

The attachment mechanisms 214 may be pin 216 and slot 218 arrangements that may fit into the detents 112 of the bone-conduction oscillator 100, as illustrated in FIG. 1, and allow the system 200 to pivot and freely slide with respect to the bone-conduction oscillator 100. The unrestricted coupling provided by the attachment mechanisms 214 allows a pressure applied by a user to be transferred through the force measurement device 260 without being mitigated, absorbed, or diverted through or by a more rigid mechanical coupling. The calibration switch aperture 220 can provide access via a pen, paper clip, or any suitable device, to a momentary switch 222 used during a calibration process and disposed within the housing 210.

The force measurement device 260 may be a bladder or any suitable device for detecting a received external force, such as a strain gauge or a load cell, among other things. For example, a bladder 260, made of a suitably compliant material, may be arranged to at least partially extend from the housing 210 such that it at least partially sits between the housing 210 and the bone-conduction oscillator 100 when the applied force indication system 200 is attached to or integrated with the bone-conduction oscillator 100. As an external force is applied to the applied force indication system 200 to couple the stimuli generated by the bone-conduction oscillator 100 to a skull of a patient, the unrestricted coupling at the attachment mechanism 214 allows the force to compress the bladder 260 between the housing 210 and the bone-conduction oscillator 100 proportionally increasing the pressure within the area sealed under the bladder 260, for example. In various embodiments, the area sealed under the bladder 260 may comprise air, fluid, or any suitable material. The bladder 260 may be composed of any suitable elastomers having a yield strength in the compressing axis that is less than a minimum pressure to be gauged, and preferably significantly less.

The applied force indication system 200 illustrated in FIG. 3 shares various characteristics with the applied force indication system 200 illustrated in FIG. 2 as described above.

FIG. 4 is a side elevation view of an exemplary applied force indication system 200 without a housing and attached to a bone-conduction oscillator 100, in accordance with an embodiment of the invention. FIG. 5 is a side perspective view of an exemplary applied force indication system 200 without a portion of the housing 210 and attached to a bone-conduction oscillator 100, in accordance with an embodiment of the invention. FIG. 6 is a side sectional view of an exemplary applied force indication system 200 attached to a bone-conduction oscillator 100, in accordance with an embodiment of the invention.

Referring to FIGS. 4-6, there is shown an applied force indication system 200 and a bone-conduction oscillator 100. The bone-conduction oscillator 100 comprises a housing 110 and a cable 120. The applied force indication system 200 comprises a housing 210, attachment mechanisms 214, a calibration switch 222, a pushbutton 230, an on/of switch 232, a microcontroller 240, a sensor 250, a force measurement device 260, indicators 270, circuit board 280, and a battery 290.

The circuit board 280 may be a printed circuit board for mechanically supporting and/or electrically connecting the components of the applied force indication system 200.

The battery 290 can be disposed on the printed circuit board 280 and is operable to provide power to the electronic components of the applied force indication system 200. In various embodiments, the battery 290 may be a 3-volt coin cell or any suitable battery for providing power to the applied force indication system 200. Additionally or alternatively, power may be provided by a wired or wireless external source. In certain embodiments, a battery can be removed from the housing 210 using an ejection mechanism 292.

The calibration switch 222 may be disposed within the housing 210 and can be used during a calibration process by accessing the switch 222 via a calibration switch aperture 220, as illustrated in FIGS. 2-3, or any suitable switch activation mechanism, for example. The calibration switch 222 can be a momentary switch, a toggle switch, or any suitable switch.

The pushbutton 230 can interact with an on/off switch 232 to power-on and power-off the applied force indication system 200. In certain embodiments, the switch 232 can be a momentary switch, a toggle switch, or any suitable switch. In various embodiments, pushbutton 230 can be a toggle, paddle, rocker, slide, or any suitable switch activation mechanism. The system may also be designed to power-on when a stimulus or other signal is detected, and to power-off after a suitable delay with the absence of a stimulus.

The force measurement device 260 may be a bladder, strain gauge, a load cell, or any suitable mechanism for detecting an applied external force. For example, a bladder 260 may be arranged to at least partially sit against the bone-conduction oscillator 100 or to a surface within the bone-conduction oscillator 100 when the applied force indication system 200 is attached to or integrated within the bone-conduction oscillator 100. As an external force is imposed on the applied force indication system 200 to couple the stimuli generated by the bone-conduction oscillator 100 to a skull of a patient, the unrestricted coupling at the attachment mechanisms 214 allows the force to compress the bladder 260 against or within the bone-conduction oscillator 100, proportionally increasing the pressure within the area sealed under the bladder 260, for example. In various embodiments, the area sealed under the bladder 260 may comprise air, fluid, or any suitable material. The attachment mechanisms 214 can be a pin 216 and slot 218 arrangements as described above in connection with FIGS. 2-3, or any suitable attachment mechanisms 214 that provides an unrestricted coupling of the applied force indication system 200 with or within the bone-conduction oscillator 100.

The sensor 250 may comprise suitable logic, circuitry, interfaces and/or code that may be operable to measure the pressure within the bladder 260. In various embodiments, the measured pressure may be updated several times per second. The measured pressure may be converted by the sensor 250 to a digital signal that is communicated to a microcontroller 240. In various embodiments, pressure measurements are performed, for example, in software, firmware, hardware, or a combination thereof. In certain embodiments, the sensor 250 can be a barometric sensor if the bladder 260 is an air bladder, a fluid sensor if the bladder 260 is a fluid bladder, or any suitable sensor that corresponds with the type of pressure measurement performed within the bladder 260, for example. In an exemplary embodiment employing a strain gauge, the sensor 250 may be omitted and/or integrated with the strain gauge circuitry.

The microcontroller 240 may comprise suitable logic, circuitry, interfaces and/or code that may be operable to convert the pressure measurement received from the sensor 250 and/or force measurement device 260 to an equivalent force measurement. In various embodiments, equivalent force measurement determinations are performed, for example, in software, firmware, hardware, or a combination thereof. For example, the microcontroller 240 can access lookup tables and calibration/correction factors, among other things, to determine the equivalent force measurement based on the pressure measurement. The microcontroller 240 can provide an indication of the equivalent force measurement via indicators 270. In certain embodiments, the sensor 250 and/or the force measurement device 260 can be integrated with the microcontroller 240, for example. In an exemplary embodiment, the conversion and processing may be performed by an external instrument with the pressure measurement transmitted by wired or wireless communication from the sensor 250 and/or force measurement device 260.

The indicators 270 can be light emitting diodes, a display screen, a receiver for providing audible speech or tones, or any suitable indicating device. For example, in an embodiment, the microcontroller 240 may illuminate a yellow light emitting diode if an equivalent force measurement that corresponds with the pressure measurement is below a pre-determined acceptable range, a red light emitting diode if the equivalent force measurement that corresponds with the pressure measurement exceeds a pre-determined acceptable range, or a green light emitting diode if the equivalent force measurement that corresponds with the pressure measurement is within the pre-determined acceptable range. In various embodiments, the pre-determined acceptable range may depend on the bone-conduction oscillator 100 being used. As an example, the pre-determined acceptable range for a B-71 bone oscillator may be between 450-550 grams of force.

The applied force indication system 200 illustrated in FIGS. 4-6 share various characteristics with the applied force indication system 200 illustrated in FIGS. 2-3 as described above.

In operation and in an exemplary embodiment of the invention, calibration of an applied force indication system 200 integrated with or attached to a bone-conduction oscillator 100 can be initiated by accessing a concealed momentary switch 222 accessible through a calibration switch aperture 220. The calibration process may be performed by applying a known weight to the applied force indication system 200. Once calibrated, a pushbutton 230 can be depressed to activate a power-on switch 232 for powering-on the battery-powered 290 applied force indication system 200, and the bone-conduction oscillator 100 with integrated or attached applied force indication system 200 may be placed against the skull of a patient to begin performing a behavioral audiometric test or an auditory brainstem response (ABR) test.

As an external force is applied by the user against the applied force indication system 200 attached to or integrated with the bone-conduction oscillator 100 to couple the stimuli generated by the bone-conduction oscillator 100 to the skull of the patient, an unrestricted coupling 214 allows an air bladder 260, or other force measurement device, of the applied force indication system 200 to compress against a top surface of the bone-conduction oscillator 100. The unrestricted coupling provided by the slot 218 in conjunction with pin 216, or other suitable attachment mechanism 214, allows the force indication system to move freely in the vertical axis as well as radially to the pin 216. The unrestricted coupling allows the pressure applied by the user to be transferred through the bladder 260 without being mitigated, absorbed, or diverted through or by a more rigid mechanical coupling. The compression of the air bladder 260 causes the pressure of the air sealed within the bladder 260 to increase proportionally. A pressure sensor 250 mounted on a circuit board 280 and located within the enclosed air bladder 260 measures the air pressure and sends the reading as a digital signal to a microcontroller 240 mounted on the circuit board 280.

The microcontroller 240 accesses a lookup table and/or calibration/correction factors to convert the pressure reading into an equivalent force measurement. Based on the equivalent force measurement, one of three different colored light emitting diodes (e.g., yellow, green, and red) 270, viewable through an indicator viewing opening or window 212 of the housing 210, is illuminated to identify whether the equivalent force measurement falls within a pre-determined range, such as 450-550 grams of force, for example. The yellow light emitting diode (LED) is illuminated for an equivalent force measurement that is below 450 grams of force. The green LED is illuminated for an equivalent force measurement that is within 450-550 grams of force. The red LED is illuminated for an equivalent force measurement that is greater than 550 grams of force.

FIG. 7 is a flow chart illustrating exemplary steps that may be utilized for providing an applied force indication to specify whether a force applied to a bone-conduction oscillator 100 is sufficient to obtain reliable audiometric and/or auditory brainstem response (ABR) hearing test results, in accordance with an embodiment of the invention. Referring to FIG. 7, there is shown a flow chart 300 comprising exemplary steps 302 through 308. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, the applied force sensor 200 coupled with the bone-conduction oscillator 100 can receive an external force. For example, the bone-conduction oscillator 100 with integrated or attached applied force indication system 200 may be pressed against the skull of a patient to begin performing a behavioral audiometric test or an auditory brainstem response (ABR) test. As the external force is applied by the user against the applied force indication system 200, a force measurement device 260, such as a bladder of the applied force indication system 200, compresses against a top surface of the bone-conduction oscillator 100, causing the pressure within the area sealed under the bladder 260 to increase proportionally. In various embodiments, the area sealed under the bladder 260 may comprise air, fluid, or any suitable material.

In step 304, a sensor 250 measures the pressure of the area sealed under the bladder 260. In certain embodiments, the sensor 250 can be a barometric sensor if the bladder 260 is an air bladder, a fluid sensor if the bladder 260 is a fluid bladder, or any suitable sensor that corresponds with the type of pressure measurement performed within the bladder 260, for example. As another example, the sensor 250 may be integrated with a strain gauge 260 or operate in conjunction with any suitable force measurement device 260. The measured pressure reading can be communicated to the microcontroller 240.

In step 306, the microcontroller 306 can determine an equivalent force measurement based on the measured pressure. For example, the microcontroller 240 may access a lookup table and/or calibration/correction factors to convert the pressure reading into an equivalent force measurement.

In step 308, indicators 270 may provide an applied force indication based on the equivalent force measurement and a pre-determined acceptable value. For example, the pre-determined acceptable value can correspond with a force or range of forces applied to a bone-conduction oscillator that is sufficient to obtain reliable audiometric and/or auditory brainstem response (ABR) hearing test results. In various embodiments, the pre-determined acceptable value may depend on the bone-conduction oscillator 100 being used. As an example, the pre-determined acceptable value for a B-71 bone oscillator may be a range between 450-550 grams of force. The indicators 270 can be light emitting diodes, a display screen, a receiver for providing audible speech or tones, or any suitable indicating device. For example, in an embodiment, the microcontroller 240 may illuminate a yellow light emitting diode if an equivalent force measurement that corresponds with the pressure measurement is below a pre-determined acceptable range, a red light emitting diode if the equivalent force measurement that corresponds with the pressure measurement exceeds a pre-determined acceptable range, or a green light emitting diode if the equivalent force measurement that corresponds with the pressure measurement is within the pre-determined acceptable range.

Additionally and/or alternatively, various embodiments provide that the measured pressure, the equivalent force measurement, and/or the applied force indication may be communicated to an external system for processing and/or application. As one example, the measured pressure can be provided to an audiometer and/or auditory brainstem response (ABR) equipment and the audiometer and/or ABR equipment can determine an equivalent force measurement based on the measured pressure. The audiometer and/or ABR equipment may be operable to present the stimulus to the bone-conduction oscillator only when the applied force is determined to be within a certain range, and/or may collect data only when the force reading is within this range. The audiometer and/or ABR equipment may also or alternatively use the force measurement to control a drive-level compensation system operable to maintain the level of signal received by the subject. The equipment may also use visual or audible prompts to provide feedback to the user about the force being applied.

Aspects of the present invention provide a method 300 and system 200 for providing an applied force indication to specify whether an external force applied to the system 200 coupled with a bone-conduction oscillator 100 is within a pre-determined acceptable range. In accordance with various embodiments of the invention, the method 300 comprises receiving 302 the external force at the applied force indication system 200. The external force causes a bladder 260 of the applied force indication system 200 to compress. The method 300 comprises measuring 304 a pressure of an area sealed within the bladder 260. The method 300 comprises determining 306 an equivalent force measurement based on the measured pressure. The method 300 comprises providing 308 the applied force indication based on the equivalent force measurement and the pre-determined acceptable range. An alternative embodiment may use a different sensor type, such as a strain gauge or a load cell, with an unrestricted mechanical attachment Various embodiments provide an applied force indication system 200 comprising a housing 210. The applied force indication system 200 comprises a bladder 260 that may be operable to compress in response to an external force received at the applied force indication system 200. The bladder 260 may comprise a sealed area. The applied force indication system 200 comprises a sensor 250 that can be operable to measure a pressure of the sealed area. The applied force indication system 200 comprises a microcontroller 240 that may be operable to determine an equivalent force measurement based on the measured pressure. The applied force indication system 200 comprises an indicator 270 operable to provide an applied force indication based on the equivalent force measurement and a pre-determined acceptable range.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system for measurement of an external force applied on a bone-conduction oscillator comprising:
   a first housing operable to receive the external force, the first housing comprising an attachment mechanism operable to provide a pivotable coupling of the first housing to a second housing of the bone-conduction oscillator;
   a force measurement device operable to measure a pressure in response to the received external force moving the first housing via the pivotable coupling with respect to the second housing of the bone-conduction oscillator to compress the force measurement device against the second housing of the bone-conduction oscillator; and
   a microcontroller operable to:
      determine an equivalent force measurement based on the measured pressure, and
      determine whether the equivalent force measurement is acceptable based on a pre-determined acceptable equivalent force measurement value.

2. The system according to claim 1, wherein the force measurement device comprises:
   a bladder comprising a sealed area, the bladder operable to compress in response to the received external force; and
   a sensor operable to measure a pressure of the sealed area.

3. The system according to claim 2, comprising an indicator operable to provide an applied force indication based on the determination of whether the equivalent force measurement is acceptable.

4. The system according to claim 1, comprising an indicator operable to provide an applied force indication based on the determination of whether the equivalent force measurement is acceptable.

5. The system according to claim 1, wherein the bone-conduction oscillator comprises the first housing, the force measurement device, and the microcontroller.

6. The system according to claim 1, wherein the attachment mechanism comprises:
   at least two slots in the first housing, and
   a pin extending through each of the at least two slots into a corresponding detent in the second housing of the bone-conduction oscillator.

7. The system according to claim 1, comprising a calibration switch configured to initiate an applied force calibration process upon activation.

8. The system according to claim 4, wherein the indicator comprises:
   a first light emitting diode that is activated when the equivalent force measurement is below the predetermined acceptable equivalent force measurement value,
   a second light emitting diode that is activated when the equivalent force measurement is above the predetermined acceptable equivalent force measurement value, and a third light emitting diode that is activated when the equivalent force measurement is one or more of equal to or within the predetermined acceptable equivalent force measurement value.

9. The system according to claim 8, wherein the first housing comprises a window that provides viewing access to the indicator.

10. The system according to claim 1, wherein the pre-determined acceptable equivalent force measurement value is a range.

11. The system according to claim 1, comprising a pushbutton and a switch, the pushbutton interacting with the switch to power-on and power-off the applied force indication system.

12. The system according to claim 1, comprising a circuit board and a battery,
wherein the circuit board electrically connects the microcontroller with the sensor and the indicator, and
wherein the battery is disposed on the circuit board and provides power to the microcontroller, the sensor, and the indicator.

13. A method for measuring an external force applied on a bone-conduction oscillator comprising:
receiving the external force at a first housing of an applied force indication system, wherein the first housing is pivotably coupled, by an attachment mechanism, to a second housing of the bone-conduction oscillator;
measuring, by a force measurement device of the applied force indication system, a pressure in response to the received external force moving the first housing via the attachment mechanism with respect to the second housing of the bone-conduction oscillator to compress the force measurement device against the second housing of the bone-conduction oscillator;
determining, by a processor, an equivalent force measurement based on the measured pressure; and
determining, by the processor, whether the equivalent force measurement is acceptable based on a pre-determined acceptable equivalent force measurement value.

14. The method according to claim 13, wherein the force measurement device is a bladder, and wherein a sensor of the applied force indication system measures the pressure of an area sealed within the bladder when the received external force causes the bladder to compress.

15. The method according to claim 14, comprising providing, by the processor, an applied force indication based on the determination of whether the equivalent force measurement is acceptable.

16. The method according to claim 13, comprising providing, by the processor, the applied force indication based on the determination of whether the equivalent force measurement is acceptable.

17. The method according to claim 13, wherein the bone-conduction oscillator comprises the first housing, the force measurement device, and the processor.

18. The method according to claim 13, wherein the applied force indication system is coupled to the second housing of the bone-conduction oscillator.

19. The method according to claim 13, wherein the pre-determined acceptable equivalent force measurement value is a range.

20. The method according to claim 13, comprising communicating the measured pressure to the processor of one or more of an audiometer or auditory brainstem response (ABR) equipment,
wherein the processor of the one or more of the audiometer or the auditory brainstem response (ABR) equipment determines the equivalent force measurement and provides bone conduction stimuli based on the equivalent force measurement and the pre-determined acceptable equivalent force measurement value.

21. A non-transitory computer readable medium having stored thereon, a computer program having at least one code section, the at least one code section being executable by a machine for causing the machine to perform steps comprising:
receiving a pressure measurement from a force measurement device of an applied force indication system in response to an external force received at a first housing of the applied force indication system, the first housing pivotably coupled by an attachment mechanism to a second housing of a bone-conduction oscillator, the received external force moving the first housing via the attachment mechanism with respect to the second housing of the bone-conduction oscillator to compress the force measurement device against the second housing of the bone-conduction oscillator;
determining an equivalent force measurement based on the measured pressure; and
determining whether the equivalent force measurement is acceptable based on a pre-determined acceptable equivalent force measurement value.

22. The non-transitory computer readable medium according to claim 21, wherein the force measurement device is a bladder, and wherein the pressure measurement corresponds with a pressure of an area sealed within the bladder when the received external force causes the bladder to compress.

23. The non-transitory computer readable medium according to claim 22, comprising providing an applied force indication based on the determination of whether the equivalent force measurement is acceptable.

24. The non-transitory computer readable medium according to claim 21, comprising providing an applied force indication based on the determination of whether the equivalent force measurement is acceptable.

25. The non-transitory computer readable medium according to claim 21, wherein the bone-conduction oscillator comprises the first housing and the force measurement device.

26. The non-transitory computer readable medium according to claim 21, wherein the pre-determined acceptable equivalent force measurement value is a range.

27. The non-transitory computer readable medium according to claim 21, comprising receiving an input to initiate an applied force calibration process.

28. The non-transitory computer readable medium according to claim 21, comprising providing bone conduction stimuli based on the equivalent force measurement and the pre-determined acceptable equivalent force measurement value.

* * * * *